United States Patent [19]

Wong

[11] Patent Number: 4,868,392

[45] Date of Patent: Sep. 19, 1989

[54] METHOD OF AND APPARATUS FOR MODULATING THE COUNTS OF A PET CAMERA

[76] Inventor: Wai-Hoi Wong, 7903 Deer Meadow, Houston, Tex. 77071

[21] Appl. No.: 190,614

[22] Filed: May 5, 1988

[51] Int. Cl.$^4$ .............................................. G01T 1/161
[52] U.S. Cl. ............................ 250/363.03; 250/363.02
[58] Field of Search ....................... 250/363.01, 363.02, 250/363.03, 363.04, 363.06, 363.09, 363.10, 370.07, 654, 659, 503.1; 378/151, 152

[56] References Cited

U.S. PATENT DOCUMENTS

| | | | |
|---|---|---|---|
| 4,389,569 | 6/1983 | Hattori et al. | 250/363.10 |
| 4,618,773 | 10/1986 | Drukier | 250/367 |
| 4,647,779 | 3/1987 | Wong | 250/367 |
| 4,677,299 | 6/1987 | Wong | 250/363.10 |
| 4,755,679 | 7/1988 | Wong | 250/363.03 |

Primary Examiner—Janice A. Howell
Assistant Examiner—Richard Hanig
Attorney, Agent, or Firm—Fulbright & Jaworski

[57] ABSTRACT

A PET camera is provided with a modulator of a material having an atomic number of at least 82. The modulator allows uses doses much higher than the PET system can handle by throttling through just the maximum allowable counting rate. As the counting activity delays, the amount of modulation is reduced so that the camera is kept counting near its maximum limit for the scanning period.

4 Claims, 3 Drawing Sheets

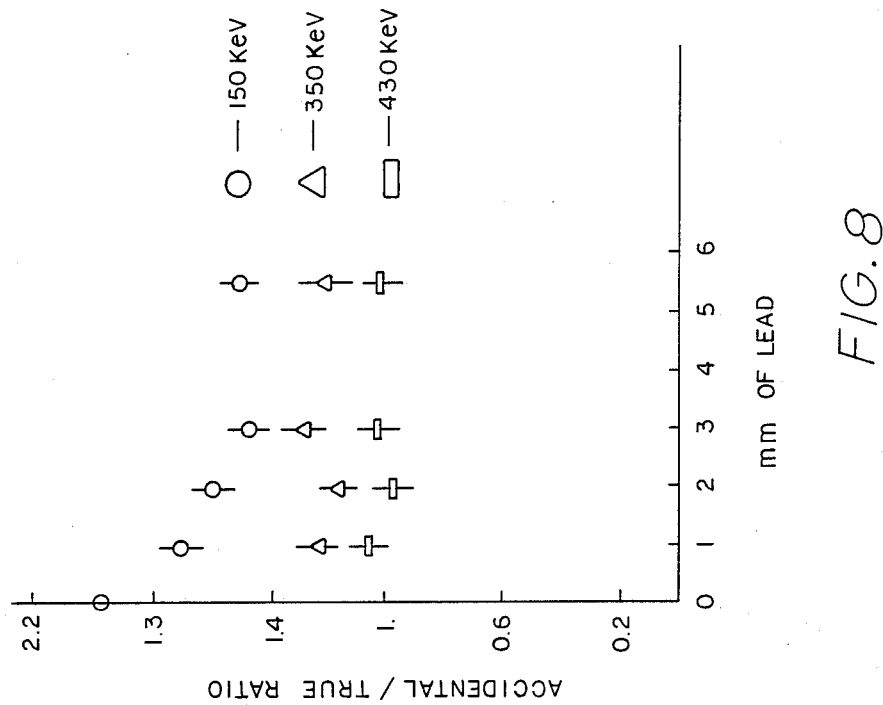
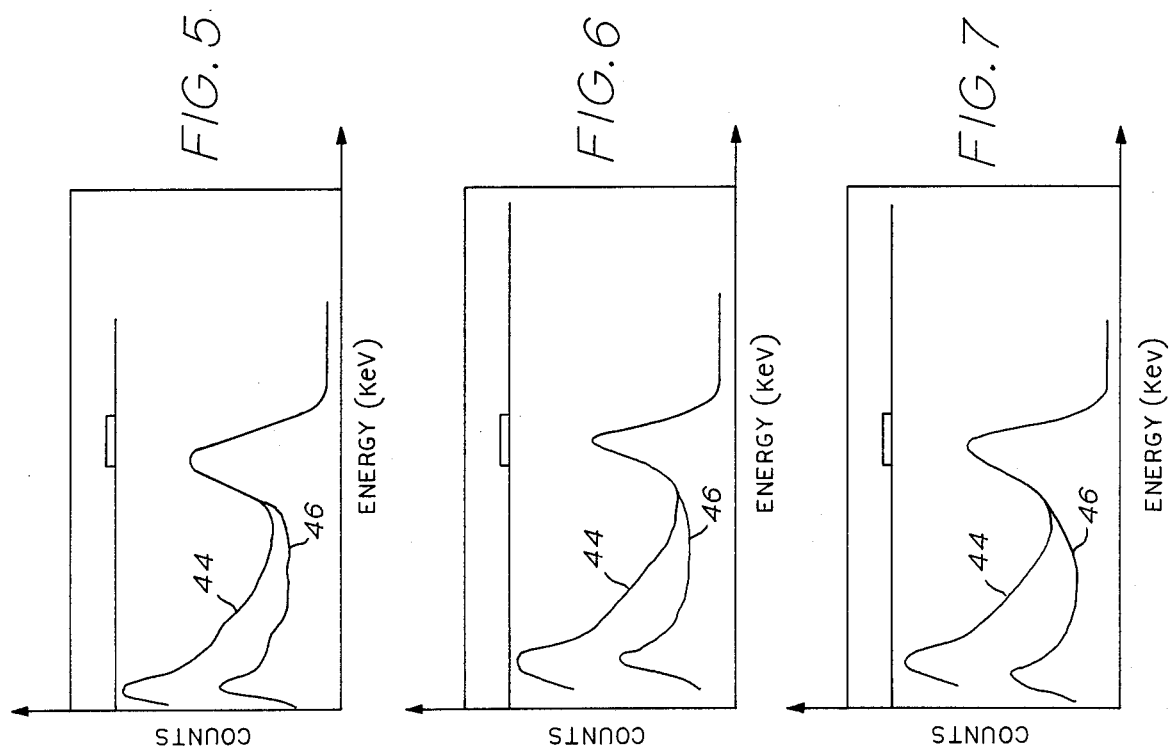

METHOD OF AND APPARATUS FOR MODULATING THE COUNTS OF A PET CAMERA

BACKGROUND OF THE INVENTION

A positron emission tomography camera (PET) is an invaluable but extremely expensive ($2,500,000) cross-sectional imaging device for in-vivo quantitative measurement of physiological and biochemical organ functions in both research and clinical environments. Positron radiopharmaceutical tracers are injected into the body. Each tracer molecule then emits two gamma-rays (511 KeV in energy). These gamma-rays are then detected by rings of tiny detectors surrounding the patient to create the cross-sectional density mapping of the tracers.

In any imaging process, from everyday 35 mm photography to a PET camera, the quality of the image depends on both the optical resolving power of the instrument and the amount of light received (photon statistics). In photography, the limiting factor is usually the resolving power of the lens/film system but not the photon statistics because the number of photons contributing to each picture-element (pixel) is extremely large that the statistical uncertainty or noise is very low. In PET or most "gamma-ray counting" imaging devices, the photon statistics is also a limiting factor in their image quality. After all, if there is enough time to count the incoming photons one by one, there cannot be too many coming in per unit time.

Recent efforts in improving the image quality of PETs are focused at improving the resolving power (intrinsic spatial resolution of the detectors) by packing smaller individual detectors into the detector rings (analogous to an insect with smaller size element in its compound eyes). However, this advance has not been accompanied by the required corresponding increase in the collected gamma-ray counts. As a result the high resolution images are noisier. Some image smoothing by pixel averaging is necessary to lower the noise in the image. But the pixel averaging procedure will lower the image resolution. Typically a 4–6 mm "intrinsic" resolution PET operates at a "usable" resolution of 6–8 mm. The difference between "intrinsic" resolution and "usable" resolution is particularly large for the very short-lived isotopes such as oxygen-15 (half-life +2 minutes) and rubidium-82 (half-life=1 minute) which decay away before enough counts are collected.

The conventional ways of increasing collected gamma-ray counts are:

(1) increasing the camera sensitivity—present cameras already have sensitivity close to 90% of the theoretical limit. Another 10% gain is very costly and hardly worthwhile. Furthermore, what is needed is a 100%–300% increase.

(2) increasing the injected radiation dose—PET cameras are also plagued by a noise called "accidental coincidences". This noise increases drastically with increased radiation level as shown in FIG. 1. All cameras can easily reach the cross-over point where the "accidentals" starts overwhelming the "true" counts. Hence, most current cameras are designed to handle a maximum count rate at which the cross-over point occurs. Further increase in the counting speed is generally a waste. Many imaging procedures already inject radiation near the cross-over point, in particular, those tracers with very short half-lives. Hence this is not a viable solution.

(3) increasing the imaging time—Again present imaging procedures are already stretching the data collection time to the practical limit of the half-life of the isotopes or other physiological and clinical requirements. Some procedures already require an hour or more of total imaging time. Hence this is also not a good solution.

(4) multiple injections—It prolongs imaging time, decreases patient throughout, and it is also more vulnerable to patient movements, physiological changes between repeated studies. Isotope recirculations from prior injection may also be a problem.

One way of improving image quality by throttling the accepted counts has been disclosed in U.S. patent application Ser. No. 06/876,066 filed June 19, 1986, now U.S. Pat. No. 4,755,679 entitled "Method and Apparatus for Maximizing Counts of a PET Camera" which uses a dynamically adjusted energy acceptance window.

The present invention is directed to the use of a modulator to modulate the incoming counts and to keep the counting rate near the maximum camera limit.

SUMMARY

The present invention is directed to a method of operating a positron emission tomography camera for measuring concentrations of positron emitting radioisotopes which measure radiation from a patient including true counts and accidental counts by providing a changeable modulator, of a material having an atomic number of at least 82, around a patient for use as a gamma-ray modulator. The method includes injecting an amount of radiation into the patient normally sufficient to initially saturate the maximum camera transfer capability and as the counting activity of the camera decays reducing the amount of modulation by the rings to keep the counting rate of the camera near its maximum limit for the scanning period. Another object of the Present invention is wherein the modulator includes a plurality of rings and modulation is reduced by removing one or more rings. Still a further object of the present invention is the improvement in a positron emission tomography camera having a plurality of detector rings positioned side-by-side around a patient area to detect radiation from the patient in which a changeable modulator is positioned between the detector rings and the patient area and the modulator is of a material having an atomic number of at least 82.

Yet a still further object of the present invention is using modulator rings of high atomic number and high density material around the patient as a gamma-ray modulator to improve the PET image quality. The modulator allows using doses much higher than the PET system can handle by allowing the detectors to receive just the maximum allowing counting rate. As the counting activity decays, one or more rings are pulled out to keep the counting rate at the maximum counting limit so that the PET is always kept counting near its maximum limit. This method and apparatus can collect up to several times more counts than normally allowed by the PET camera.

Other and further objects, features and advantages will be apparent from the following description of a presently preferred embodiment of the invention, given for the purpose of disclosure and taken in conjunction with the accompanying drawings.

BRIEF DESCRIPTION OF THE DRAWINGS

FIG. 5 illustrates the amount of scattered gamma suppression using the present invention, FIGS. 6 and 7 are graphs illustrating the difference between unmodulated and modulated scatters for a 20 cm object and a 30 cm object, respectively, and FIG. 8 is a chart illustrating the coincidence measurement for the accidental and true counts as a function of modulator thickness and energy acceptance windows.

DESCRIPTION OF THE PREFERRED EMBODIMENT

Figure 1:
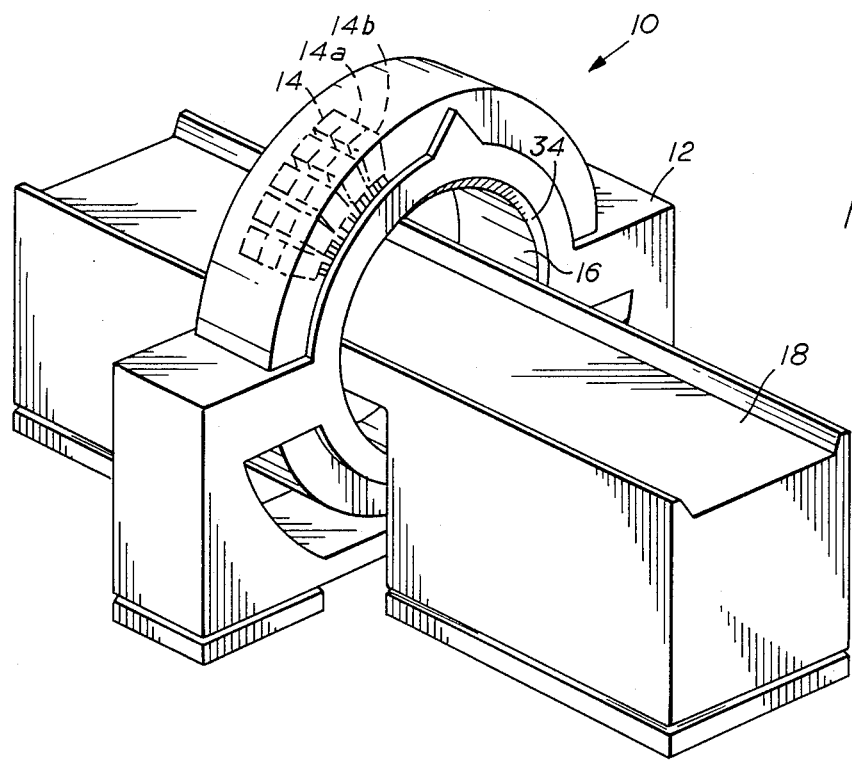
FIG. 1 is a perspective elevational view of the positron tomography camera of the present invention.

Referring now to the drawings, and particularly to FIG. 1, the reference numeral 10 generally indicates a positron emission tomography (PET) camera having a support 12, a plurality of planes of detectors, here shown as rings, positioned side-by-side and surrounding a patient area to detect radiation therefrom. The patient area 16 may include a patient bed 18 for supporting a patient. In a PET camera, a positron isotope such as Rb82, is injected into the patient, each positron isotope atom then emits two gammas simultaneously and back-to-back. The detectors then capture these gammas to produce an image of the tracer distribution.

Figure 2:
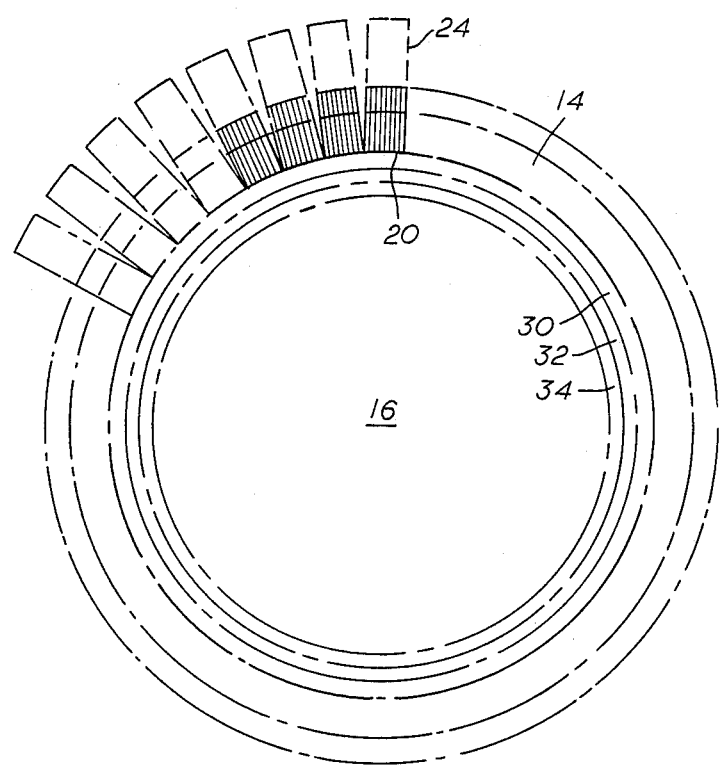
FIG. 2 is an enlarged schematic cross-sectional view of one plane of detectors and the modulator of the present invention around a patient area.

Each plane, such as three planes 14, 14a and 14b, provide a straight on slice and interplane slices between adjacent planes. Any desirable number of planes or rings 14 may be used. As best seen in FIG. 2, a single ring, such as 14, includes a plurality of scintillation crystals 20 and light detectors 24. The crystals may be any suitable type, such as BGO crystals, and the light detectors 24 may be any suitable type, such as photomultiplier tubes or silicon advance photodiodes. The above-named description of the PET camera 10 is generally conventional.

Figure 3:
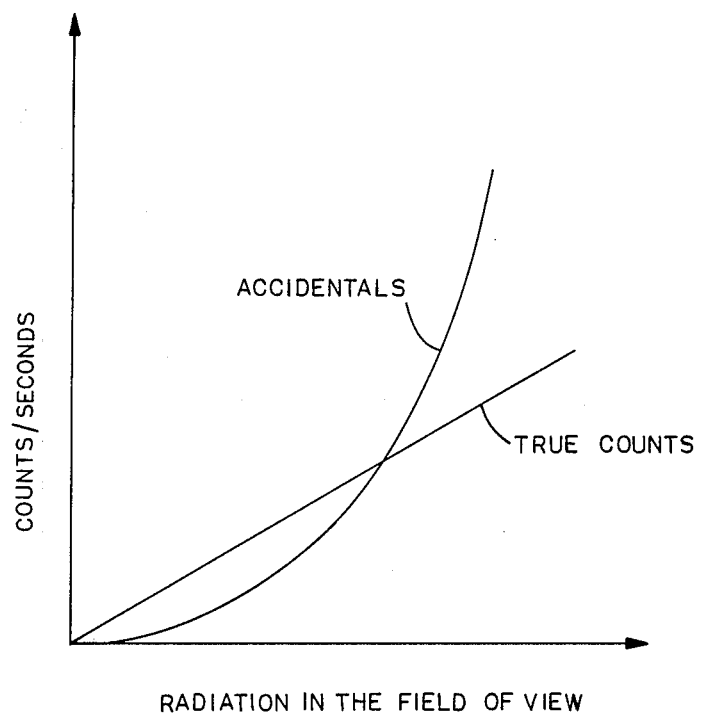
FIG. 3 is a graph illustrating the relationship between accidental counts and true counts with increased radiation level.

However, as best seen in FIG. 3, the detectors of the PET camera 10 in addition to receiving true counts also are plagued by accidental counts. As shown, the accidental counts can easily reach the cross-over point where the accidentals start overwhelming the true counts. Hence most current cameras are designed to handle a maximum count rate at which the cross-over point occurs.

Figure 4:
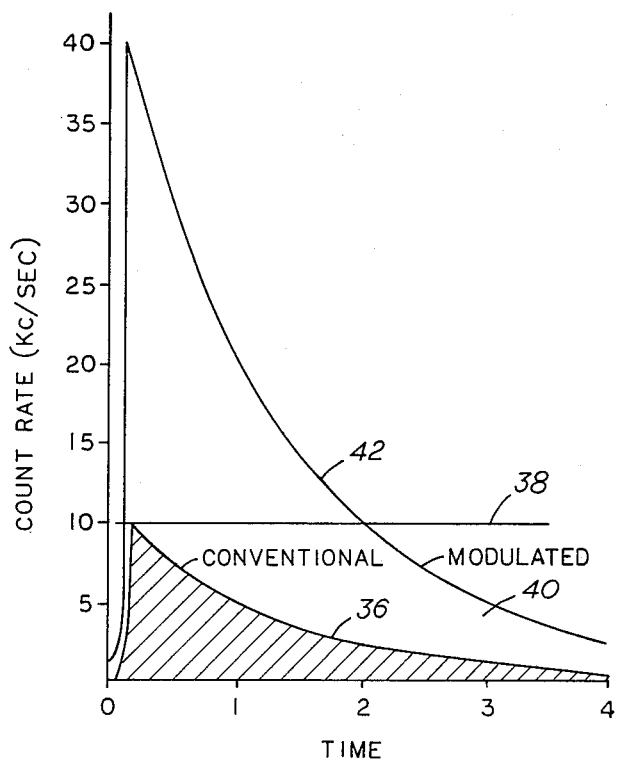
FIG. 4 is a graph illustrating the comparison of measured counts between a prior art camera and the camera used in the present invention.

The present invention is directed to increase the total gamma-ray counts collected in an imaging section by surrounding the patient with a changeable modulator here shown as a plurality of concentric rings 30, 32 and 34 as best seen in FIG. 2 which are positioned between the patient area 16 and the crystals 20 and detectors 24. The modulator rings 30 and 32 and 34 (any desired number may be used) are of a material having a high atomic number, that is, at least 82, for example, lead. This may seem like a paradox (killing counts to collect more counts). The concept of the present invention is best illustrated in FIG. 4 in which the camera has a maximum allowable count rate of 10,000 counts/second per image slice. In conventional data collection, many procedures require an injection dose such that the initial counts will be slightly below the maximum counting limit of the camera. This provides a count-time graph 36 which provides a maximum count activity which is less than the maximum data transfer rate 38 of the camera and the data collection continues timewise until the activity data rate is insignificantly low. However, when the radiation decays away, as illustrated by graph 36, either from radio-decay or biological-decay, the maximum counting capability of the camera is hardly utilized. The camera detection system is idling most of the time as illustrated in FIG. 4 from time 2 to time 4. The total counts collected for the entire conventional procedure is the area under the graph 36. Now, with a much higher injected dose, the total count rate may reach 40,000 counts/sec. which far exceeds the maximum data processing rate 38 of the camera. However, if a changeable modulator such as a stack of ring modulators 30, 32, 34 are inserted into the camera to surround the patient, the total count rate can be lowered to the maximum 10,000 counts/sec. limit. As the radiation decays at later time, one or more modulator rings 30, 32 and 34 will be pulled out of the camera sequentially and as necessary to keep the camera counting at its maximum rate all the time. The total count collected (in area 40 and also under graph 36) will be much more than the conventional data collection (under graph 36) at which the camera is idling much of the time. Since in PET imaging the shape of the time-activity curve needs to be known, the shape of the upper curve 42 (FIG. 2) which was distorted by modulation has to be restored. This can be easily done by renormalization multiplications to account the ring attenuation factor which is known.

The above illustration shows the advantage of modulation or throttling incoming gammas in a simple way. There are in fact two more advantages. Firstly, the "accidental" counts which increase drastically with radiation level are dominated by the scattered gamma-ray scattered by the patient body. These scattered gammas are less energetic than the unscatter true counts at 511 KeV energy. These accidental counts only contribute to noise in the image and occupy valuable count processing time of the detection system. The less energetic nature of the scattered gammas make them much more readily absorbed by the modulating material than the unscattered true gammas. However, the ring can also generate its own scattered gammas. But with the high atomic number (Z), at least 82, and high density material chosen here, the amount of scattered gamma suppression is far greater than the generation. FIG. 5 shows the incident gamma energy spectra (histograms) from a simulated patient body. The upper curve 44 is unmodulated and the lower curve 46 is modulated by 5.5 mm of lead-bismuth alloy. The peak on the right is the 511 KeV unscattered gammas. For an identical number of 511 KeV gamma incident onto the detectors 24, the unmodulated spectrum has a much larger amount of the lower energy scattered gamma than the spectrum with modulation. Hence using the modulation rings also decrease the severity of the "accidental" noise in the image. Secondly, with the detection system exposed to less useful counts, there will be more time allocated to detect the true counts. This is because the detector is dead for a period of time (1–2 microseconds) after the detection of one event. If a second gamma arrives sooner than that time, the second event will be lost. The same dead time also exists for the detector electronics. Therefore if there is a 50% decrease in the scatter gamma reaching the detector, there will be that much more free time to process the true gamma and results in an additional increase in true counts on top of the count increase from the gamma throttling process described The present invention can be summarized as follows:
(1) suppresses the detrimental "accidental" noise in the image at high injection dosage.
(2) increases the total counts collected to lower the photon statistical noise in the image by operating the camera at the maximum rate for the entire imaging period.
(3) decreases the detection dead time to allow another effective increase in true counts collected in the final image.

The multiple increase in collected counts and the additional suppression in the "accidental" noise combines to lower the noise of PET substantially. This allows the current high resolution PET camera to produce a higher "usable" resolution which is closer to the "intrinsic" resolution because less image smoothing is needed to lower the noise. This invention also presents a very inexpensive and easy way to improve the image quality or resolution of any existing old camera without any internal hardware or software modification.

Hence, a ring or rings of high atomic number, at least 82, and high density modulator is proposed here to modulate the incoming count, which will have the same effect as the dynamic-energy-window method with the added advantage of lowering the gamma flux impringing onto the detectors. The most obvious reservation to this method is the possibility of increasing the scatter gamma which in turn increases the accidental coincidences. This is indeed true, if we are imaging a point source. But, since we are imaging an extended source which introduce a large amount of scatters, a high Z modulator in fact suppresses more patient scatters than generates them. This study examines such issues by measuring the scatter, accidental and true in 20 and 30 cm uniform source with a coincidence measurement simulating a neuro-camera. Modulators of lead and bismuth with thickness from 1-5.5 mm has been measured. The energy spectra exit from 5.5 mm of Pb and incident onto the detector are shown in FIG. 6 for a 20 cm object and FIG. 7 for a 30 cm object. The upper curves are the regular unmodulated spectra, and the lower curves are the modulated spectra. Hence, the scatters are about 50% less with the modulator for similar photopeak counts. The coincidence measurement for the accidental and true is shown in FIG. 8 as a function of modulator thickness and energy acceptance windows. Hence the modulator in fact improves the data quality, lowers the detector/electronics dead time in processing less bad counts in addition to increasing total counts collected like the dynamic-energy-window method.

The present invention, therefore, is well adapted to carry out the objects and attain the ends and advantages mentioned as well as others inherent therein. While a presently preferred embodiment of the invention has been given for the purpose of disclosure, numerous changes in the details of construction and arrangement of parts will be readily apparent to those skilled in the art and which are encompassed within the spirit of the invention and the scope of the appended claims.

What is claimed is:

1. The method of operating a positron emission tomography camera for measuring concentrations of positron emitting radioisotopes which measure radiation from a patient including true counts and accidental counts comprising, providing a changeable modulator of a material having an atomic number of at least 82, around a patient for use as a gamma ray modulator for allowing only the maximum allowable counting rate through the modulator, injecting an amount of radiation into the patient normally sufficient to initially saturate the maximum camera transfer capability, as the counting activity of the camera decays, reducing the amount of modulation to keep the counting rate of the camera near its maximum limit for the scanning period.

2. The method of claim 1 wherein the modulation is performed by a plurality of rings and is reduced by removing one or more rings.

3. In a positron emission tomography camera having a plurality of detector rings positioned side-by-side around a patient area to detect radiation from the patient, the improvement comprising, a changeable modulator positioned between the detector rings and the patient area for use as a gamma ray modulator for allowing only the maximum allowable counting rate through the modulator, said modulator being of a material having an atomic number of at least 82.

4. The apparatus of claim 3 wherein the modulator includes, a plurality of concentric rings.

* * * * *

UNITED STATES PATENT OFFICE
CERTIFICATE OF CORRECTION

Patent No. 4,868,392                  Dated September 19, 1989

Inventor(s) Wai-Hoi Wong

It is certified that error appears in the above-identified patent and that said Letters Patent is hereby corrected as shown below:

Column 1, line 62, before "cameras" insert -- present --

Column 5, line 6, after "described" insert -- earlier. --

Signed and Sealed this

Eighteenth Day of September, 1990

Attest:

HARRY F. MANBECK, JR.

*Attesting Officer*            *Commissioner of Patents and Trademarks*